United States Patent [19]

Frackelton

[11] Patent Number: 5,529,574
[45] Date of Patent: Jun. 25, 1996

[54] METHOD AND APPARATUS FOR TREATMENT OF THE PROSTATE

[76] Inventor: James P. Frackelton, 963 Cahoon Rd., Westlake, Ohio 44145

[21] Appl. No.: 291,128

[22] Filed: Aug. 16, 1994

Related U.S. Application Data

[63] Continuation-in-part of Ser. No. 933,381, Aug. 21, 1992, abandoned.

[51] Int. Cl.⁶ ........................................................ A61F 7/12
[52] U.S. Cl. .............................................. 604/49; 604/22
[58] Field of Search ................................. 604/21, 22, 49; 606/32, 33, 39, 45; 607/96, 97, 98

[56]  References Cited

U.S. PATENT DOCUMENTS

| | | |
|---|---|---|
| 3,428,046 | 4/1965 | Remer et al. . |
| 3,825,015 | 7/1974 | Berkovits . |
| 3,842,841 | 10/1974 | Brighton et al. . |
| 3,933,147 | 1/1976 | DuVall et al. . |
| 3,942,536 | 3/1976 | Mirowski et al. . |
| 4,010,755 | 3/1977 | Preston . |
| 4,304,239 | 12/1981 | Perlin . |
| 4,683,890 | 8/1987 | Howson . |
| 4,750,488 | 6/1988 | Wuchinich et al. ................. 604/22 |
| 4,785,828 | 11/1988 | Maurer . |
| 4,909,263 | 3/1990 | Norris . |
| 4,955,377 | 9/1990 | Lennox et al. . |
| 4,998,933 | 3/1991 | Eggers et al. . |
| 5,080,660 | 1/1992 | Beulna . |
| 5,191,883 | 3/1993 | Lennox et al. . |
| 5,199,442 | 4/1993 | Sesgh et al. ................. 128/788 |
| 5,220,927 | 6/1993 | Astrahan et al. . |
| 5,234,004 | 8/1993 | Hascoet et al. . |
| 5,249,585 | 10/1993 | Turner et al. . |

FOREIGN PATENT DOCUMENTS

| | | |
|---|---|---|
| 2547203 | 12/1984 | France . |
| 1947412 | 11/1980 | Germany . |
| 363495 | 7/1966 | U.S.S.R. . |
| 0721110 | 3/1980 | U.S.S.R. . |
| 1220673 | 3/1986 | U.S.S.R. . |

Primary Examiner—Manuel Mendez
Attorney, Agent, or Firm—Watts Hoffmann Fisher & Heinke

[57]  ABSTRACT

A catheter for providing low level electrical stimulation to a prostate gland to relieve the deleterious effects of prostatic disorders that respond to low level electrical stimulation is provided in combination with a power supply adapted to provide low voltage direct current or low voltage, low frequency alternating current of less than about 30 kHz. The catheter comprises an elongated flexible body having a forward end and a rearward end, said forward end having a therapeutic region adapted for positioning within a prostatic urethra. The therapeutic region comprises a portion of the length of said flexible body rearward of said forward end defined by a plurality of electrodes disposed about the circumference of said flexible body in spaced relation to each other throughout the length of said therapeutic region.

32 Claims, 2 Drawing Sheets

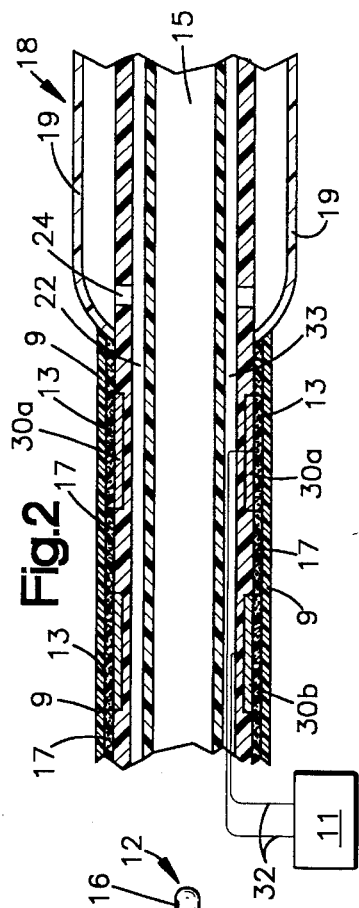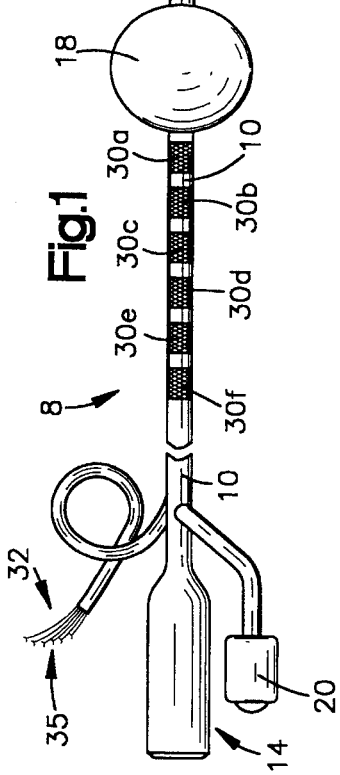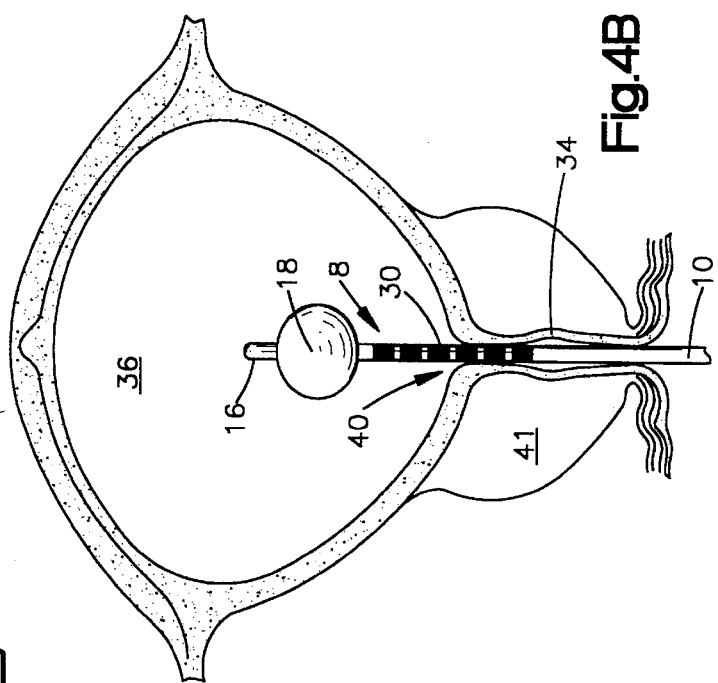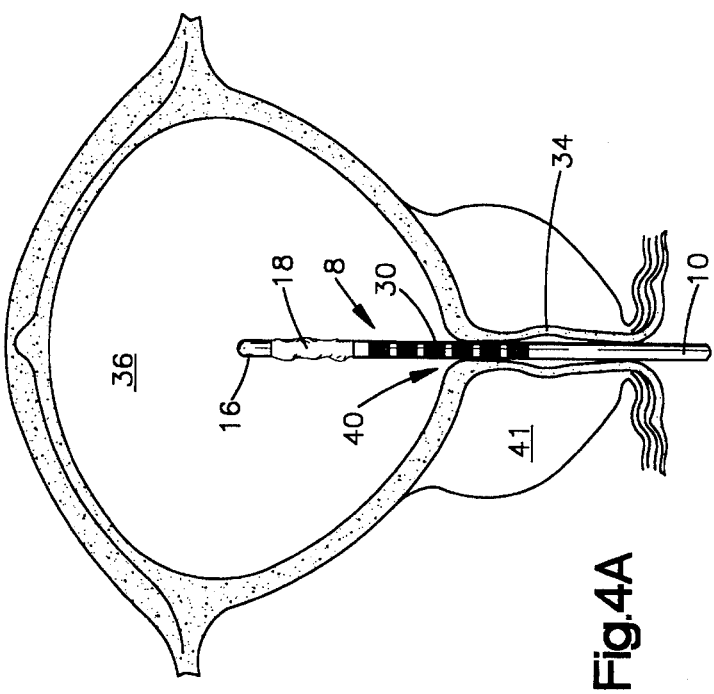

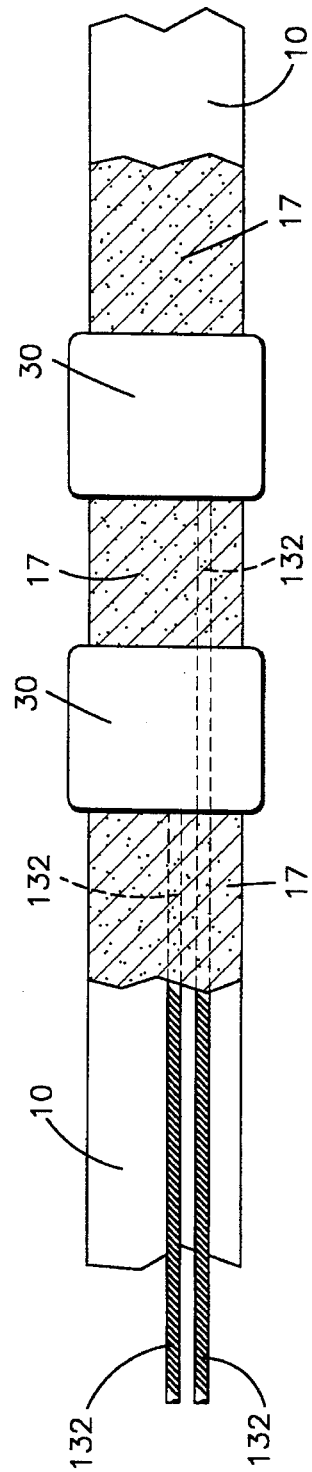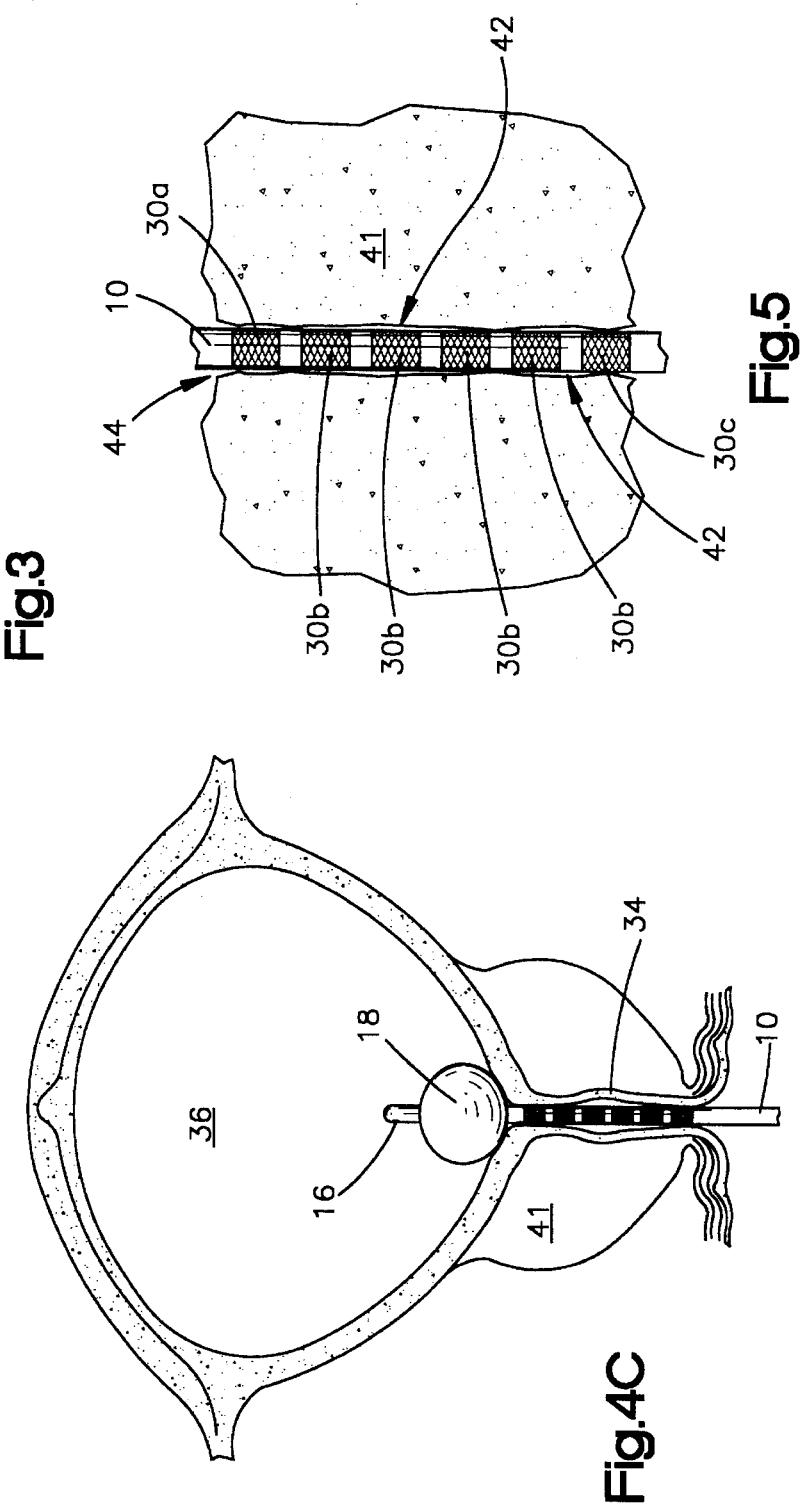

METHOD AND APPARATUS FOR TREATMENT OF THE PROSTATE

This application is a continuation-in-part of application Ser. No. 07/933,381, filed Aug. 21, 1992, now abandoned.

BACKGROUND OF THE INVENTION

The invention relates generally to a method and apparatus for treatment of a prostate gland. More specifically, the invention relates to a catheter for applying low level electrical stimulation to a prostate gland in order to relieve the deleterious effects of prostatic diseases such as benign prostatic hypertrophy and hyperplasia.

The normal prostate is a gland surrounding the urethra that has been likened to a chestnut in size and shape. In humans, the median lobe of the prostate frequently, in older men, hypertrophies and rises into the bladder thereby blocking the urethral orifice resulting in obstruction to micturition. For reasons not fully understood, both the fibromuscular and glandular elements often increase in size with age so that about two thirds of all males reaching the age of seventy have some degree of obstruction. The glands near the urethra are chiefly involved in hypertrophy, and those in the median lobe hypertrophy first.

Experiments suggest that testosterone entering the prostate cells converts to dihydrotestosterone and stimulates prostaglandin (PG) synthesis and release to inhibit further testosterone binding to the prostate. Klein L. A. and Stoff J. S., Prostate, 4(3):247–51 (1983). With aging, PG synthesis becomes less efficient, resulting in decline of putative inhibitory effect of PG on cell growth and increase in testosterone binding to prostatic cells. Combined effects may produce unrestrained protein synthesis and cell growth resulting in benign prostatic hyperplasia and hypertrophy. Whatever the cause, the problem is prolific and non-invasive, inexpensive, effective treatments are needed. Cancer of the prostate has become the most common cancer diagnosed in American males and the second most common cancer related cause of death in males. Approximately 38,000 die of prostate cancer in the United States each year and studies show that it occurs to some degree in 30% of males over the age of 50 and in 67% of those between 80 and 89.

Current methods of treatment for benign prostatic hypertrophy and hyperplasia include digital palpitation through the rectum to purge the prostate of stagnated prostatic fluid and other deleterious fluids that accumulate in the gland. This procedure is somewhat painful and only temporarily relieves the condition. Various pharmaceutical treatments have also been developed for these benign prostatic ailments with varying levels of success. Pharmaceuticals are, however, expensive, have side effects and may not be suitable for all patients if other health conditions require incompatible drug treatments. For cancer of the prostate, invasive surgical removal of the gland is still the commonly accepted treatment.

DESCRIPTION OF THE INVENTION

The invention provides a simple and effective apparatus for relieving the deleterious effects of prostatic disorders that are responsive to low level non-invasive electrical stimulation. The invention also provides a relatively inexpensive and effective method for treating prostatic disorders such as benign prostatic hypertrophy, hyperplasia and cancer, and to relieve the effects thereof, such as obstruction to micturition. In accordance with the invention there is provided a novel combination of a power supply adapted to provide low voltage direct current or low voltage, low frequency alternating current, and a catheter for the treatment of prostatic conditions that respond to low level electrical stimulation. Electrical stimulation by the catheter can induce the prostate to contract and purge itself of accumulated fluids more completely than digital palpitation, thereby reducing the frequency of treatment. It can also set up a therapeutic electric field in the prostate. It is believed that the catheter and procedures associated therewith involve less pain than digital palpitation and result in much greater therapeutic value when a low frequency electric field is induced.

In one embodiment the catheter of the invention comprises an elongated flexible body having a forward end and a rearward end, the forward end having a therapeutic region adapted for positioning within a prostatic urethra. The therapeutic region comprises a portion of the length of the flexible body rearward of the forward end defined by at least one, and preferably a plurality of electrodes disposed in or on the body in spaced relation to each other throughout the length of the therapeutic region. Preferably annular electrodes are disposed about the circumference of the flexible body. A power supply is connected to the electrodes for selectively energizing the electrodes. The catheter is adapted to enable current to flow from any one of said electrodes to any other of said electrodes or to simply create a potential difference between any number of the electrodes and the surrounding tissue.

In another embodiment, the body is a hollow tube that includes a small opening near the forward end and an inflatable balloon rearward of the opening near the forward end but forward of the therapeutic region. The body also includes means for supplying the inflatable balloon with an inflation medium such as air or water. The therapeutic region comprises a portion of the length of the flexible body rearward of the inflatable balloon near the forward end defined by a plurality of annular electrodes disposed about the circumference of the flexible body in spaced relation to each other throughout the length of said therapeutic region. The electrodes are preferably spaced about 3 to 4 mm apart and a first of the electrodes is disposed about 4 to 5 mm rearward of the inflatable balloon.

In a preferred embodiment, the catheter is coated with a so called z-axis material which restricts the direction of current flow. In accordance with the invention this coating allows current to flow both in a direction normal to the catheter body and in the radial direction about the catheter body. This enhances the therapeutic effect of the catheter by forcing current to travel outward from the catheter into the surrounding tissue instead of following the shortest distance along the catheter body directly from one electrode to the other.

Importantly, the catheter of the invention is coupled to a power supply adapted to provide low voltage direct current or low voltage, low frequency alternating current of less than about 30 kHz. In this way, the novel combination of the inventive catheter and low voltage, low frequency power source cooperate to create a therapeutic current and/or electric field in the prostate. Preferably, the coupling of the power source and catheter creates a low frequency AC current of less than about 10 kHz. Still more preferably between about 20 Hz and 1000 Hz. While the voltages applied by the power source can be on the order of about 70 volts, they are preferably kept between about 0.5 and 35 volts. Anything over about 30 to 35 volts tends to become very uncomfortable. The pain and heat associated with higher voltages require the use of anesthetics. Advantageously, the low voltages associated with the invention do not require anesthetic. In order to minimize pain and heat production, the current associated with the foregoing signals is also kept very low. Preferably, less than about 50 mA.

In a method of relieving the deleterious effects of prostatic disorders according to the invention, electrodes are positioned within a prostatic urethra to enable,, the electrodes to deliver a low level electrical current and/or field within the prostate. By creating a potential difference between the electrodes, a current is delivered through the prostate that causes the prostate to contract thereby purging itself of excess fluids associated with various prostatic disorders. In one embodiment, the electrodes of the catheter can be used in conjunction with an electrode or electrodes mounted on the exterior of the body. Here, one or more of the electrodes on the catheter act as the anode or cathode with respect to the external electrodes, depending upon the desired current and therapeutic effect.

In a preferred method according to the invention, the electrodes are positioned so that one electrode is in contact with the prostatic urethra proximal to the upstream end thereof, i.e., proximal to the bladder, another electrode is in contact with the prostatic urethra proximal to the downstream end thereof, and at least one additional electrode is in contact with the prostatic urethra therebetween.

Optimum positioning is preferably accomplished by positioning the first of said electrodes about 4 mm behind an inflatable balloon disposed at the forward end of a catheter, and the remainder of said electrodes spaced equally about 3 to 4 mm apart rearward of said first electrode and form a therapeutic region about 30 to about 60 mm long. The catheter is inserted into the urethra and fed into the body until it enters the bladder. Preferably, this is determined by disposing a hole in the forward end of the catheter so that entry of the catheter into the bladder is indicated by a discharge of urine from the catheter. The balloon is then inflated and the catheter withdrawn until the balloon abuts against the bladder wall at the orifice of the prostatic urethra into the bladder. The first electrode will thus correspond generally to the upstream end of the prostatic urethra and the remainder of the electrodes will be disposed generally evenly throughout the remainder of the prostatic urethra. Low level electric current can then be effectively delivered throughout the prostate or to any desired portion thereof. Of course the catheter of the invention may be used in combination with other treatments, such as drug therapies, heat and the like.

These and other advantages and a fuller understanding of the invention will be had from the following detailed description of the invention and accompanying drawings.

BRIEF DESCRIPTION OF THE DRAWINGS

FIG. 1 is a stylized perspective of a catheter according to the invention.

FIG. 2 is a stylized cross-sectional view of a segment of a therapeutic region of a catheter according to the invention.

FIG. 3 is a stylized perspective of a segment of a therapeutic region of a catheter according to the invention.

FIGS. 4A—4C are stylized anterior cross-sections of a bladder and prostate showing the progressive positioning steps of a catheter according to an embodiment of the invention.

FIG. 5 is a stylized cross-section showing the positioning of a therapeutic region of a catheter according to the invention within a prostatic urethra.

DETAILED DESCRIPTION OF THE PREFERRED EMBODIMENTS

Urinary catheters and the materials from which they may be made are not new and the catheter of the invention may be made by methods and from materials known to those of ordinary skill in the art of catheter manufacture. Typically, a catheter comprises a long tubular body formed from flexible plastic or resinous materials such as rubber, cellulose acetate, nylon, ethyl cellulose, polyether-polyamide copolymers, combinations thereof and the like, although any flexible material known to those of skill in the art for use in medical or surgical applications is contemplated as being suitable for the invention. Conductors, such as electrodes, suitable for delivering non-intrusive low level electric current to animal tissues are also known in the art and include, for example, conductive plastic, metal electrodes, conductive ink and the like. The invention resides in equipping a catheter with conductors in a specific configuration and electrically addressable manner to enable effective positioning within a prostatic urethra and then coupling the catheter to a suitable power supply adapted to provide therapeutic low level electrical stimulation to a prostate gland, or portion thereof, for relieving prostatic ailments and their deleterious effects such as urinary blockage and associated obstruction to micturition.

FIGS. 1 and 2 show a preferred catheter 8 according to the invention comprising a generally tubular, flexible body 10 having a forward end 12 and a rearward end 14. The body depicted has a hollow interior 15 and can vary significantly in length as is known to those of ordinary skill in the art. The forward end 12 includes a hole 16 opening into the hollow interior 15 of the catheter body 10. Near the forward end 12 of the catheter there is an inflatable balloon 18, shown inflated. The balloon comprises a thin sheath 19 of flexible material, typically the same material as that which forms the body, disposed integrally with the body 10 about the outer circumference thereof. As shown, the inflatable balloon cooperates with a connector 20 through the channel 22, seen best in FIG. 2, disposed in the body 10. By injecting a syringe at connector 20 air is forced through the channel 22 and into the balloon 18 through the opening 24 to inflate the balloon. Alternatively, another fluid source, such as a syringe filled with water, may be connected to the catheter at 20 and used to inflate the balloon.

Near the forward end 12 of the body 10, rearward of the balloon 18 a therapeutic region of the catheter is defined by a plurality of conductive electrodes 30 disposed along the length of the catheter about the outer circumferential surface of the body 10. As shown, the therapeutic region comprises a series of six electrodes 30a–e evenly spaced from each other rearward of the balloon. As will be described in more detail below, in the preferred embodiment the first electrode rearward of the balloon is disposed about 4 mm therefrom for purposes of optimum positioning. The remainder of the electrodes are spaced about 4 mm apart. The therapeutic region, defined by the length between the first and last electrodes rearward of the balloon, corresponds generally to the average length of a prostatic urethra of a subject of the age and condition to be treated. Thus, in the case of the typical human adult male, the length of the therapeutic region will be between about 30 to about 60 min. In rare cases, a very large hypertrophied prostate may yield a prostatic urethra as long as 90 mm.

The electrodes 30 cooperate with a power source, shown schematically at 11, via wires 32 disposed in a channel 33 in the body 10. The wires 32a–e terminate externally of the catheter with connectors 35 adapted to connect to a suitable power source. In the simplest preferred construction, one wire 32 is connected to each of the electrodes 30a–e, via channel 33. For treatment, the wires are connected to a power supply adapted to selectively switch each of the electrodes to a higher or lower potential than each of the other electrodes, creating a potential difference therebetween. Thus, for example, the power supply may apply a positive voltage to any one of the electrodes 30 and at the same time switch any of the remaining electrodes to a lower potential, e.g., ground. Since the prostate and surrounding tissue will conduct electricity, current will flow from the positive electrode, through the prostate, to an electrode of lower potential, e.g., the grounded electrode.

In a preferred embodiment, the catheter includes a coating adapted to prevent current from flowing directly from one electrode to another axially along the catheter body 10, referred to herein as a z-axis coating 9, shown in FIG. 2. Although this material prevents current to flow in the axial direction along the catheter, current can freely flow in the x and y directions, normal to the catheter body and radially around the catheter body respectively. This allows current to flow from one electrode to another but prevents or inhibits it from traveling directly along the catheter body from one electrode to another. In this way, the maximum amount of electricity will be forced to travel from one electrode, out and away from the catheter body through the surrounding tissue, to a second electrode. Suitable materials or coatings which permit electricity to travel in all but one direction are commercially available. One such material is manufactured and sold by Shin-Etsu Polymer America, Inc., under the trademark Shin-Flex. This material comprises a thin, flexible sheet consisting of alternating segments of conducting and insulating solid silicone rubber.

The z-axis coating 9 may be secured to the outer circumference of the catheter 10 by means of an adhesive. Since current must be able to flow from the electrodes, it is important that when adhesive is applied over the electrodes, the adhesive is electrically conductive. Similarly, it is important that any adhesive between electrodes be non-conductive. Otherwise, the current would simply flow from one electrode to another underneath the z-axis coating. In one such embodiment, shown conceptually in FIG. 2, both electrically conductive adhesive 13 and electrically non-conductive adhesive 17 may be used, the former coating the electrodes and the later the catheter body. Alternatively, one or the other may be used. For example, the structure shown in FIG. 3 shows only nonconductive adhesive 17. In most instances, this should be sufficient to secure the z-axis coating over the catheter. Electrically conductive adhesives are commercially available from, for example, The 3 M company.

It is to be understood that the catheter depicted in the drawings is not to scale and only illustrates a preferred embodiment and mode of operation of the invention, and that other catheter configurations would be suitable. For example, an inflatable balloon need not be used but is preferred for positioning purposes. Similarly, the number, width and spacing of the electrodes may be varied within the scope of the invention, so long as they define a therapeutic region suitable for treating a prostate as disclosed herein. Thus, in the case of the typical human adult male, the number, spacing and size of the electrodes may vary significantly as long as the therapeutic region corresponds generally to the 30–60 mm length of the prostatic urethra. Still further, as conceptually shown in FIG. 3, the electrodes 30 need not be recessed into the catheter body 10, and conductors 133, need not be internally mounted as in FIGS. 1 and 2. In this embodiment, since the electrodes 30 and conductors 133 are mounted on the outer surface of the catheter body 10, provision must be made to keep the electrodes 30 and conductors 133 insulated from one another. To this end, the conductors 133 may be small gauge insulated wires as shown, or similar conductive channels that are otherwise insulated from each other and the electrodes under which they pass. It is also important in this :embodiment to use the z-axis coating. In addition to restricting the direction of current flow, this ensures a relatively uniform outer circumference for purposes of comfort and insertability. As shown in FIG. 3, the coating may be secured by means of a non-conductive adhesive 17. However, to ensure the best electrical contact between the electrodes and the z-axis coating the electrodes preferably are also coated with an electrically conductive adhesive 13 as seen in FIG. 2.

The power supply 11 is adapted to provide a low voltage direct current or a low voltage, low frequency alternating current. The preferred power supply can provide voltage to any of the electrodes and switch any of the other electrodes to a lower potential such as ground. In this way, the electrodes can be selectively charged so that current can flow from any of the electrodes to any of the other electrodes. Similarly, only some of the electrodes may be charged so that the current or electric field only effects a portion of the surrounding prostate. Alternatively, one or more of the electrodes can be used in conjunction with electrodes mounted externally on the subjects body. Depending upon the desired treatment, the electrodes of the catheter may be used as the anode or the cathode with respect to such an externally mounted electrode. Still further, an equal potential may be applied to the electrodes to create a potential difference between the electrode and the surrounding tissue. Suitable electronics for the desired switching and signal production are well within the skill in the art. For example, one such power supply is manufactured by Physiodynamics Inc., under the tradename TheraStim, Model 100. Another such power supply, called a DC Treatment Processor, is manufactured and sold by Tekniska Röntgencentralen AB, Stockholm, Sweden.

The power supply delivers low level non-invasive electrical stimulation to the tissue in contact with or surrounding the electrodes of the catheter. Several forms of electrical stimulation are currently known to those of ordinary skill in the art. These include single polarity, low frequency alternating signals, interference currents consisting of two or more independent medium frequency currents that penetrate the treatment area and interfere with each other to produce a low frequency, and multi-phasic signals produced with simultaneous high and low frequencies to create a multi-phase signal with polarity. The nature of the electrical signal may be adjusted depending on the nature of the ailment and treatment desired. However, in all cases the signal according to the invention will be a low voltage direct current or a low voltage, low frequency alternating current of less than about 30 kHz. In the case of alternating current, the coupling of the power source and catheter preferably creates a low frequency AC current of less than about 10 kHz. Still more preferably between about 20 Hz and 1000 Hz. Some specific frequencies that are believed to be particularly useful are 20, 666, 670, 727 and 2127 Hz. The current associated with the foregoing signals is also kept low, e.g., less than about 50 mA. For example, a 666 Hz signal at 32 volts is only about 30 mA, and a 10,000 Hz signal at 23 volts is only about 4.4 mA.

The voltages applied by the power source are preferably less than about 70 volts, still more preferably between about 0.5 and 35 volts. Voltages in excess of about 35 volts tend to create discomfort and an associated need for anesthetic. When treated at the preferred voltages of the invention, there is advantageously no need for anesthetic. The specific voltage used may vary depending on the nature of the treatment. For example, if simple contraction and purging of the prostate is all that is desired, the characteristics of the signal are not critical as long as suitable contraction is obtained. Simple direct current in the range of 1.0 to 15 V will typically suffice for this purpose. However, the importance of the signal characteristics increases when therapeutic treatment beyond simple contraction and purging is desired as described in Nordenström, M.D., Biologically Closed Circuits, Nordic Medical Publications (1983), incorporated herein by reference.

As noted above, in the preferred embodiment the instant catheter includes an inflatable balloon for positioning purposes. The preferred method is illustrated in FIGS. 4A–4C. The catheter 8 is inserted into the body through the urethra. The catheter is fed into the body until it passes through the prostatic urethra 34 and into the bladder 36. When the catheter includes an opening or hole 16, a discharge of urine may be detected when the catheter enters the bladder, indicating the approximate position of the forward end 12. While the opening 16 is not necessary to the invention, it is preferable because the discharge of urine is a good indicator that the catheter has entered the bladder and is ready for the next step in the procedure. At this point in the method the catheter is slightly beyond its final position, the inflatable balloon 18 having passed through the prostatic urethra 34 and at least partially into the bladder 36. The balloon 18 is then inflated, as seen in FIG. 4B, and the catheter withdrawn until the inflated balloon stops against the interior wall/opening 40 of the prostatic urethra 34 into the bladder. The catheter is now properly positioned with the annular electrodes 30 of the therapeutic region of the catheter spaced along the prostatic urethra 34.

While the size of the prostate varies widely from subject to subject depending upon age, the relative emptiness of the bladder, the progression of the hypertrophy and the progression of treatment, the first electrode rearward of the inflated balloon should generally correspond to the up stream end, i.e., the end proximal to the bladder, of the prostatic urethra using this method and the catheter described above. FIG. 5 is a stylized representation of a prostate 41 and prostatic urethra 42 having an upstream end 44 proximal to the bladder and a downstream end 46 distal to the bladder. Optimum spacing of the electrodes occurs where an electrode 30a is in contact with the prostatic urethral wall at its end 44 proximal to the opening into the bladder, another electrode or electrodes 30b is/are spaced evenly along the middle region of the prostatic urethra and another electrode 30c downstream therefrom at the approximate beginning of the prostatic urethra 46, distal to the bladder. Optimum electrode spacing as shown enables the effective stimulation of nearly all of the prostate.

Since, as noted above, the size of the prostate can very widely depending on the subject, the relative progression of the hypertrophy or hyperplasia and numerous other factors, the number of electrodes spaced along the therapeutic region of the catheter can also vary. For example, four, six, eight or more electrodes can be used. Similarly, the width of each electrode can vary from a single thin line to a band of conducting material 8 to 10 millimeters wide.

While not wanting to be bound by theory, a specific electric input can give a detectable feedback that will vary depending upon its location in the body. For example, resistance will increase or decrease depending upon the tissue through which the current must pass to go from one electrode to another. Similarly, the bodies own electric potential changes in regions of damage, such as tumors, hypertrophied tissues and the like. In some instances this is referred to as the current of injury and the difference in potential from surrounding tissues is measurable. For example, the tissue in the region of a tumor will be more negative or positive than the surrounding tissue, although only to a minute degree. In one embodiment, a given feedback signal, such as resistance, can be used to indicate the proximity of the therapeutic region of the catheter of the invention to the prostate or prostatic urethra, since in a hypertrophied or cancerous prostate the resistance or potential of that region will differ from, for example, the bladder. A series of test pulses can be used to determine the approximate size of the prostate and location of the therapeutic region with respect thereto. By employing the test pulses, the electrode proximal to the upstream end of the prostatic urethra and the electrode proximal to the downstream end of the prostatic urethra can be determined based on their relative feedback. These two electrodes define the outer ends of the effective therapeutic region of the catheter that will be used in the treatment. This allows for optimum positioning and electrical stimulation of the prostate without the need for the inflatable balloon.

Once the catheter is positioned electrical stimulation can be effectively delivered to a prostate. The electric signal can cause a hypertrophied prostate to contract and purge itself of accumulated fluids thereby relieving the associated obstruction to micturition. The magnitude of the pulse can vary to tolerance, with pain and damage from heat of course being desirably avoided. Typically, voltages in the range of 0.5 to 5.0 volts may be used, although different electrical signals and magnitudes may be used to impart more significant therapeutic effects, as noted above. Low frequency alternating current, on the other hand, not only sends electric current through the prostate, but also sets up a therapeutic electric field in the prostate.

Many variations and modifications of the invention will be apparent to those of ordinary skill in the art in light of the foregoing detailed disclosure. Therefore, it is to be understood that, within the scope of the appended claims, the invention can be practiced otherwise than as specifically described.

What is claimed is:

1. In combination, a power supply adapted to energize non-ablating, non-cutting electrodes with electromagnetic energy of a low voltage direct current or low voltage, low frequency alternating current of less than about 30 kHz, and a catheter for the treatment of prostatic conditions that respond to low level electrical stimulation coupled to said power supply, said catheter comprising:

a) an elongated flexible body having a forward end and a rearward end, said forward end having a therapeutic region adapted for positioning within a prostatic urethra;

b) said therapeutic region comprising a portion of the length of said flexible body rearward of said forward end defined by at least one non-ablating, non-cutting electrode disposed on an outer circumference of said flexible body; and, c) conductors connecting said electrodes to said power supply, whereby said power supply and said catheter cooperate to create a therapeutic low frequency electric field and/or electrical current in said prostate.

2. The combination according to claim 1 wherein said therapeutic region comprises six electrodes about 6 mm in width and spaced about 4 mm apart.

3. The combination according to claim 1 wherein said body is a hollow tube including a small opening near said forward end and an inflatable balloon rearward of said opening near said forward end forward of said therapeutic region, and means for supplying said inflatable balloon with an inflation medium.

4. The combination according to claim 3 including a plurality of electrodes wherein a first said electrodes is disposed about 4–5 mm rearward of said inflatable balloon and each additional electrode is spaced about 4 mm apart rearward therefrom.

5. The combination according to claim 1 wherein said power supply is adapted to selectively energize said electrodes.

6. The combination according to claim 1 wherein said power supply is adapted to energize said electrodes with a low voltage, low frequency alternating current of less than about 10 kHz.

7. The combination according to claim 1 wherein said power supply is adapted to energize said electrodes with a low voltage, low frequency alternating current of from about 20 kHz to 1000 Hz.

8. The combination according to claim 1 wherein said power supply is adapted to energize said electrodes with a low voltage direct current of from about 0.5 volts to about 35 volts.

9. In combination, a power supply adapted to energize non-ablating, non-cutting electrodes with electromagnetic energy of a low voltage direct current or low voltage, low frequency alternating current of less than about 30 kHz, and a catheter for the treatment of prostatic conditions that respond to low level electrical stimulation coupled to said power supply, said catheter comprising:

a) an elongated flexible body having a forward end and a rearward end, said forward end having a therapeutic region adapted for positioning within a prostatic urethra;

b) said therapeutic region comprising a portion of the length of said flexible body rearward of said forward end defined by a plurality of non-ablating, non-cutting electrodes disposed in an outer circumference of said flexible body in spaced relation to each other throughout the length of said therapeutic region; and, c) conductors connecting said electrodes to said power supply, whereby said power supply and said catheter cooperate to create a therapeutic low frequency electric field and/or electrical current in said prostate.

10. The combination according to claim 9 wherein said therapeutic region comprises six electrodes about 6 mm in width and spaced about 4 mm apart.

11. The combination according to claim 9 wherein said body is a hollow tube including a small opening near said forward end and an inflatable balloon rearward of said opening near said forward end forward of said therapeutic region, and means for supplying said inflatable balloon with an inflation medium.

12. The combination according to claim 11 wherein a first of said electrodes is disposed about 4–5 mm rearward of said inflatable balloon and each additional electrode is spaced about 4 mm apart rearward therefrom.

13. The combination according to claim 9 wherein said power supply is adapted to energize said electrodes with a low voltage, low frequency alternating current of less than about 10 kHz.

14. The combination according to claim 9 wherein said power supply is adapted to energize said electrodes with a low voltage, low frequency alternating current of from about 20 Hz to 1000 Hz.

15. The combination according to claim 9 wherein said power supply is adapted to energize said electrodes with a low voltage direct current of from about 0.5 volts to about 35 volts.

16. A catheter according to claim 1 or 9 wherein said therapeutic region is about 36 to about 60 mm long.

17. A method of treating prostatic conditions that respond to low level electrical stimulation comprising:

a) positioning at least one non-ablating, non-cutting electrode within a prostatic urethra; and, b) energizing said electrode with electromagnetic energy of a low voltage direct current or a low voltage, low frequency alternating current of less than about 30 kHz, so as to create a potential difference between said electrode and another electrode, or between said electrode and surrounding tissue.

18. The method according to claim 17 comprising positioning a first electrode proximal to an upstream end of said prostatic urethra, a second electrode proximal to a downstream end of said prostatic urethra, and disposing at least one additional electrode therebetween.

19. The method according to claim 18 comprising creating said potential difference between two of said electrodes.

20. The method according to claim 17 wherein said low voltage, low frequency alternating current is less than about 10 kHz.

21. The method according to claim 17 wherein said low voltage, low frequency alternating current of from about 20 Hz to 1000 Hz.

22. The method according to claim 17 wherein said low voltage direct current is between about 0.5 volts to about 35 volts.

23. A method of treating prostate conditions that respond to low level electrical stimulation comprising:

a) feeding a catheter having a plurality of non-ablating, non-cutting electrodes disposed thereon into a prostatic urethra, b) positioning said plurality of electrodes within a prostatic urethra; and c) energizing at least one of said electrodes with electromagnetic energy of a low voltage direct current or a low voltage, low frequency alternating current of less than about 30 kHz, to create a potential difference between said electrode and another electrode, or between said electrode and surrounding tissue.

24. The method according to claim 23 further comprising positioning a first of said electrodes proximal to an upstream end of said prostatic urethra, another of said electrodes proximal to a downstream end of said prostatic urethra, and disposing at least one additional electrode therebetween.

25. The method according to claim 23 comprising creating said potential difference between two of said electrodes.

26. The method according to claim 23 wherein said low voltage, low frequency alternating current is less than about 10 kHz.

27. The method according to claim 23 wherein said low voltage, low frequency alternating current of from about 20 Hz to 1000 Hz.

28. The method according to claim 27 wherein said low voltage, low frequency alternating current is less than about 10 kHz.

29. The method according to claim 27 wherein said low voltage, low frequency alternating current of from about 20 Hz to 1000 Hz.

30. The method according to claim 27 wherein said low voltage direct current is between about 0.5 volts to about 35 volts.

31. The method according to claim 23 wherein said low voltage direct current is between about 0.5 volts to about 35 volts.

32. A method of treating prostatic conditions that respond to low level electrical stimulation comprising:

a) feeding a catheter having a plurality of non-ablating, non-cutting electrodes disposed thereon and an inflatable balloon disposed forward of said electrodes into a body through a urethra and into a bladder;

b) inflating said inflatable balloon;

c) positioning said catheter so that said balloon abuts against a wall of said bladder at an opening of a prostatic urethra into said bladder, whereby said plurality of electrodes are positioned within said prostatic urethra; and, b) energizing at least one of said electrodes with electromagnetic energy of a low voltage direct current or a low voltage, low frequency alternating current of less than about 30 kHz to create a potential difference between said electrode and another electrode, or between said electrode and surrounding tissue.

* * * * *